United States Patent
Hermescec

(10) Patent No.: US 10,071,501 B2
(45) Date of Patent: Sep. 11, 2018

(54) CHEMICALLY MODIFIED WOOD AND NON-WOOD PRODUCTS AND METHODS FOR THE PRODUCTION THEREOF

(71) Applicant: Branko Hermescec, Zibo (CN)

(72) Inventor: Branko Hermescec, Zibo (CN)

(73) Assignees: Ling Ling Zhang, New South Wales (AU); Branko Hermescec, Shandong (CN)

( * ) Notice: Subject to any disclaimer, the term of this patent is extended or adjusted under 35 U.S.C. 154(b) by 185 days.

(21) Appl. No.: 14/898,459

(22) PCT Filed: Apr. 1, 2015

(86) PCT No.: PCT/CN2015/075713
§ 371 (c)(1),
(2) Date: Dec. 14, 2015

(87) PCT Pub. No.: WO2015/154635
PCT Pub. Date: Oct. 15, 2015

(65) Prior Publication Data
US 2016/0144531 A1    May 26, 2016

Related U.S. Application Data

(63) Continuation of application No. PCT/CN2014/075206, filed on Apr. 11, 2014.

(51) Int. Cl.
| | | |
|---|---|---|
| *B27K 3/08* | (2006.01) | |
| *B27K 3/34* | (2006.01) | |
| *B27K 7/00* | (2006.01) | |
| *A61L 2/00* | (2006.01) | |
| *A61L 9/00* | (2006.01) | |
| *B27K 3/02* | (2006.01) | |
| *B27K 3/15* | (2006.01) | |
| *C07F 5/04* | (2006.01) | |
| *C09D 185/04* | (2006.01) | |

(52) U.S. Cl.
CPC .............. *B27K 3/343* (2013.01); *A61L 2/00* (2013.01); *A61L 9/00* (2013.01); *B27K 3/0214* (2013.01); *B27K 3/08* (2013.01); *B27K 3/15* (2013.01); *B27K 3/34* (2013.01); *B27K 7/00* (2013.01); *C07F 5/04* (2013.01); *C09D 185/04* (2013.01)

(58) Field of Classification Search
CPC ........ B27K 3/343; B27K 3/0214; B27K 3/08; B27K 3/15; B27K 3/34; B27K 7/00; C07F 5/04; C09D 185/04
USPC ......................................................... 428/541
See application file for complete search history.

(56) References Cited

U.S. PATENT DOCUMENTS 7,858,203 B2 * 12/2010 Schneider .............. B27K 3/156
                                                              252/388
8,158,206 B2 *  4/2012 Van Rhijn .............. B27K 3/153
                                                              427/393

FOREIGN PATENT DOCUMENTS

| CN | 101913181 | * | 12/2010 |
| CN | 101913181 A | | 12/2010 |
| NZ | 538393 | * | 10/2006 |
| NZ | 538393 A | | 10/2006 |
| WO | WO 2007/147804 A1 | | 12/2007 |
| WO | WO2007147804 | * | 12/2007 |

OTHER PUBLICATIONS

International Search Report dated Jun. 17, 2015 in PCT/CN2015/075713.
International Written Opinion dated Jun. 17, 2015 in PCT/CN2015/075713.

\* cited by examiner

*Primary Examiner* — Leszek Kiliman
(74) *Attorney, Agent, or Firm* — Swanson & Bratschun, L.L.C.

(57) ABSTRACT

Provided is a process for chemically modifying wood or non-wood comprising: (a) impregnating said wood or non-wood with an aqueous composition comprising an acid polymerization catalyst; (b) impregnating the wood or non-wood product from step (a) with 3-furfuryl borate ('3-FB'); and (c) subjecting the wood product from (b) for a time and under conditions to affect polymerization of the 3-FB. Modified wood and non-wood products are also provided.

22 Claims, 5 Drawing Sheets

CHEMICALLY MODIFIED WOOD AND NON-WOOD PRODUCTS AND METHODS FOR THE PRODUCTION THEREOF

CROSS REFERENCE TO RELATED APPLICATIONS

This application is a 35 U.S.C. § 371 national phase application of International Application Serial No. PCT/CN2015/075713, filed Apr. 1, 2015 (WO 2015/154635). PCT/CN2015/075713 claims priority to International Application Serial No. PCT/CN2014/075206, filed on Apr. 11, 2014, which is hereby incorporated by reference in its entirety for all purposes as if fully set forth herein.

FIELD OF THE INVENTION

The present invention relates to modified wood and non-wood products and processes for their production. In particular the invention relates to methods of chemically modifying wood or non-wood products such as hardwood (softwood) as well as non-wood products such as bamboo, modified wood/non-wood products derived from such methods, and novel reagents which are to be used as wood and non-wood modifiers.

BACKGROUND TO THE INVENTION

Many of the most valuable rainforest hardwood resources are in danger of extinction due to extensive logging. It is not viable to attempt to replace slow-growing hardwood tree species and maintain a vibrant logging industry. Consequently many countries have placed bans on the logging and export of such species, and have resorted to fast growing plantation softwood species and some non-wood species like bamboo in order to maintain their timber industry. Notwithstanding such bans unscrupulous loggers and exporters continue to harvest species such as Ebony (very dense blackwood from species of genus *Diospyros*, family of Ebenaceace) and Rosewood (family Leguminosae). Ebony species under threat include *Diospyros ebenum* (India and Sri Lanka), *Diospyros crassiflora* (Africa), *Diospyros celebica* (Indonesia) and *Diospyros gracilipes* (Madagascar). One reason for this continued trade is that the plantation softwood timber is not comparable to the hardwood species in terms of performance, such as structural and engineering characteristics, for instance, water resistance, impact resistance, density, dimensionally stability, and so on.

In an aspect the present invention is directed to the chemical treatment of plantation grown wood and non-wood (such as plantation grown softwood and sapwood, and even bamboo), with the aim of producing a modified wood non-wood product which shares many of the qualities of natural hardwood timber, thus reducing the desire for the natural hardwood.

SUMMARY OF INVENTION

In one aspect the invention provides a process for chemically modifying wood or non-wood comprising:
(a) impregnating said wood or non-wood with an aqueous composition comprising an acid polymerisation catalyst;
(b) impregnating the wood or non-wood product from step (a) with 3-furfuryl borate ('3-FB'); and
(c) subjecting the wood or non-wood product from (b) for a time and under conditions to affect polymerisation of the 3-FB.

In an embodiment the modification process is applied to wood and preferably softwood.

In an embodiment the modification process is applied to non-wood and preferably Kraft paper.

In a further aspect the invention provides a chemically modified wood product derived from softwood which has been produced by the polymerisation of 3-furfuryl borate within said softwood.

In a further aspect the invention provides a chemically modified non-wood product derived from Kraft paper which has been produced by the polymerisation of 3-furfuryl borate within said Kraft paper.

In a further aspect the invention provides a chemically modified wood product which has been impregnated with 3-furfuryl borate.

In a further aspect the invention provides 3-furfuryl borate for use as a wood modifier.

In a further aspect the invention provides a method of preparing 3-furfuryl borate ('3-FB') comprising the steps of:
(i) reacting furfuryl alcohol ('2-FM') or 3-furfuryl methanol ('3-FM') with boric acid; and
(ii) removing water produced during the reaction of (i).

DETAILED DESCRIPTION OF PREFERRED EMBODIMENTS OF THE INVENTION

Figure 1:
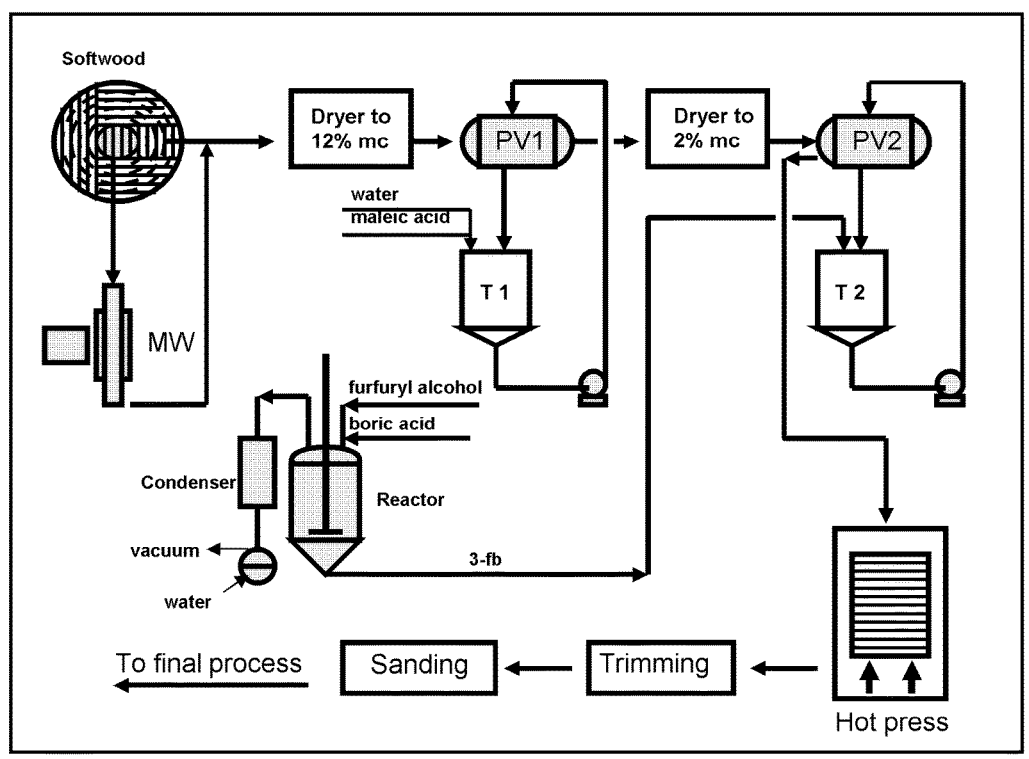
FIG. 1—Process flow diagram of a process according to the present method.

In the first step of the process the wood or non-wood is impregnated with an aqueous composition comprising an acid polymerisation catalyst. Prior to this step however it will be appreciated that softwood, for instance, may be subjected to one or more pretreatment steps. For instance in a preferred pretreatment step softwood is dried to reduce the moisture content (MC). Preferably the MC of the softwood prior to being subjected to the first step is less than 20%, and more preferably less than 15%. Most preferably the MC of the softwood is about 12% or less.

In an embodiment which involves the use of Kraft paper, preferably the MC is less than 5%, for example about 4%, about 3%, about 2%, or about 1%.

In a further embodiment which involves the use of Kraft paper, the MC is substantially 0%. Accordingly in an embodiment the pretreatment step involves the removal or substantial removal of water prior to the impregnating step.

This pretreatment drying step may be conducted using drying apparatus known in the art, including the use of commercial drying kilns and bay air drying over a period of time in an environment which is relatively humidity free.

Accordingly in another aspect the invention provides a process for chemically modifying softwood comprising:
(i) drying the softwood to reduce its moisture content;
(ii) impregnating said softwood with an aqueous composition comprising an acid polymerisation catalyst;
(iii) impregnating the wood product from step (ii) with 3-FB; and
(iv) subjecting the wood product from (iii) for a time and under conditions to affect polymerisation of the 3-FB.

"Wood" as used herein refers to both "softwood" and "hardwood".

"Softwood" as used herein refers to permeable or semi-permeable wood, timber or lumber, (often derived from conifers) which have a hardness typically not exceeding 3500 N and densities generally below 500 kg/m$^3$. Conifer species which are a common source of softwood include pine (for instance radiata pine), fir, spruce, cedar and hemlock (tsuga). The term also includes sapwood which is the outermost younger xylem layer in a growing tree. This is to be contrasted with heartwood. It will be appreciated that the methods described herein may also be applied to relatively impermeable woods to which has been applied a pretreatment step or steps to increase the permeability of the wood. For instance, a permeability enhancing pretreatment step may include microwave or steam treatments.

"Non-wood" refers to perennial evergreens of the true grass family (Poaceae), tribe bambuseae, in which the dicotyledonous woody xylem is absent. The absence of growth wood causes stems to be columnar rather than tapering, examples of non-wood includes bamboo. In the context of the present invention the term "non-wood" also refers to Kraft paper which is paper or paperboard (cardboard) produced from chemical pulp which has been treated by the Kraft process. Kraft paper as used herein also encompasses Sack Kraft paper or just sack paper which is a porous Kraft paper with high elasticity and high tear resistance, designed for packaging products with high demands for strength and durability.

As used herein the term "impregnated" or "impregnation" refers to the act of incorporating a chemical into the wood or non-wood structure wherein the resultant wood or non-wood product is said to be chemically loaded. For instance, and without wishing to be bound by theory, it is believed that in the impregnating steps disclosed herein the acid polymerisation catalyst composition and 3-FB will diffuse into the cell walls of the permeable or semi-permeable softwood. Any impregnation step disclosed herein may be either (i) uniformly achieved so that the chemical exists completely and wholly throughout the cellulosic structure of the wood or (ii) may diffuse substantially throughout the structure of the wood.

The first step in the process may be carried out with the use of any acid polymerisation catalyst. The acid polymerisation catalyst may be selected from those which are soluble or partly soluble in water to enhance the impregnation step. Water soluble or part soluble acid polymerisation catalysts may be organic or inorganic in nature and may include solubilising agents such as emulsifiers to assist solubility and hence impregnation. Examples of suitable acid polymerisation catalysts include multifunctional carboxylic acids such as maleic acid, itaconic acid (methylenesuccinic acid), and 1,2,3,4-butanetetra carboxylic acid (BTCA).

Preferably the acid polymerisation catalyst is maleic acid.

Preferably the composition comprising the acid polymerisation catalyst is an aqueous composition comprising between 1-10% w/w of the acid polymerisation catalyst. More preferably the concentration is between 2-5% w/w.

Preferably the acid polymerisation catalyst does not cause the pH of the resultant wood or non-wood product to decrease such that this engenders undesirable brittleness to the finished/modified wood or non-wood product. On the other hand, if the pH is too high, it may inhibit the polymerisation reaction.

Preferably the impregnation step is capable of loading, for instance, the wood, with the acid polymerisation catalyst from about 15% to 30% (based on the dry weight of the wood or non-wood).

The impregnation of the acid polymerisation catalyst may be carried out by any known process including absorption methods utilising capillary action (e.g., dipping and soaking) or using vacuum and/or pressure techniques.

In a preferred method the impregnation step involves the systematic treatment of the wood or non-wood under various pressures, for example, a vacuum-pressure-vacuum system. In this embodiment, the impregnating step comprises applying an initial vacuum to the wood or non-wood followed by the application of pressure in the presence of the aqueous acid polymerisation catalyst solution. Preferably, the vacuum is applied at a pressure of from −90 to −95 kPa. Preferably the pressure applied to the wood or non-wood to facilitate impregnation of the acid polymerisation catalyst composition is from about 200 to about 1,000 kPa, more preferably at least 300 kPa.

In the next step the wood or non-wood product which has been initially impregnated with the acid polymerisation catalyst is subsequently impregnated with 3-FB.

Prior to this subsequent impregnation step the wood or non-wood product may be preferably dried again to reduce the moisture content (MC) even further. Preferably the MC of the wood or non-wood product at this point is less than 10%, and more preferably less than 5%. Most preferably the MC of the wood or non-wood product prior to treatment with 3-FB is about 2% or less.

Accordingly, in a further aspect the invention provides a process for chemically modifying softwood comprising:
(i) drying the softwood to reduce its moisture content;
(ii) impregnating said softwood with an aqueous composition comprising an acid polymerisation catalyst;
(iii) drying the wood product from step (ii) to reduce its moisture content;
(iv) impregnating the wood product from step (iii) with 3-FB; and
(v) subjecting the wood product from (iv) for a time and under conditions to affect polymerisation of the 3-FB.

The "3-FB" may be prepared by reacting furfuryl alcohol ('2-FM') or 3-furfuryl methanol ('3-FM') (both $C_5H_6O_2$) with boric acid ($H_3BO_3$) or $B(OH)_3$. Synonyms for furfuryl alcohol include 2-furyl methanol or 2-furancarbinol. Synonyms for 3-furfuryl methanol include: 3-(hydroxymethyl) furan; 3-furancarbinol; 3-furfuryl alcohol; 3-furylcarbinol; 3-furylmethanol; 3-furylmethyl alcohol and furan-3-yl methanol. Synonyms for boric acid include: hydrogen borate, boracic acid, orthoboric acid or acidum boricum.

Preferably the reagents (2-FM or 3-FM and boric acid) are added together at room temperature. Preferably about 3 mol of 2-FM or 3-FM is reacted with 1 mol of boric acid. Preferably the reaction is constantly stirred and maintained so that it does not exceed 85° C. Water may be intermittently or continuously collected to drive the reaction to completion or near completion. This can be achieved by the use of, for instance, a fitted condenser unit and water collection flask. The reaction may be monitored by intermittently extracting samples and determining the extent of 2-FM or 3-FM consumption (e.g. by MS or GC).

The resultant 3-FB may be further purified or used straight from the reactant mixture. Preferably though the 3-FB is processed to remove excessive amounts of water which may otherwise inhibit the polymerisation step.

The various reactions contemplated above are represented as follows:

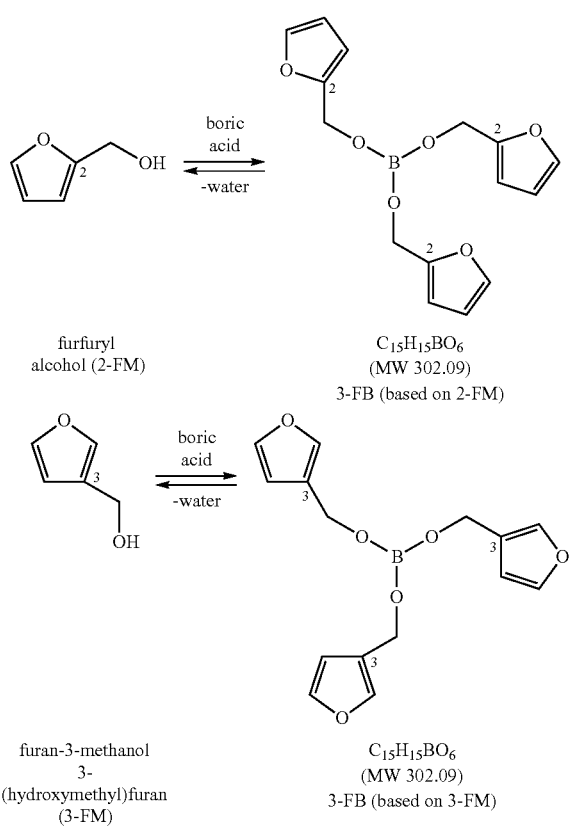

Water is removed to drive the reaction to completion (or to the right).

In a preferred embodiment the reaction involves 2-FM, and thus forms the 3-FB based on 2-FM.

It will be appreciated from the above that reference to "3-FB" includes the borate esters of both 2-FM and 3-FM.

The 3-FB impregnation step may be conducted so as to facilitate chemical loading of the wood or non-wood, preferably at a loading of from about 15% to 30% (based on the dry weight of the wood or non-wood). In a preferred embodiment, the impregnating step comprises applying an initial vacuum to the wood or non-wood followed by the application of pressure in the presence of the furfuryl alcohol solution. Preferably, the vacuum is applied at a pressure of from −90 to −95 kPa. Preferably, the pressure applied to the wood to facilitate impregnation of 3-FB is from about 200 to about 1,000 kPa, more preferably at least 300 kPa.

In another embodiment the method optionally includes a 3-FB diffusion step which is preferably conducted over a period of from about 3 to 5 days at ambient pressure and temperature. The diffusion step is preferably such that the wood, for instance, swells up to about 4-8% per volume relative to the volume of the original wood sample. It will be understood by those in the art that the amount of swelling of the wood will be somewhat dependent on the density of the wood and that denser wood may be expected to swell more than less dense wood.

The methods described above may also include one or more additional impregnation or diffusion steps to include pesticides (such as fungicides, insecticides, etc), wood preserving agents, colouring pigments or fire retardant agents. One of the advantages of the present invention is that with the use of 3-FB the boron acts to protect against insects, fungi, marine borers, etc. Furthermore, the final treated wood product which is quite dry prevents (or at least minimises) any microorganism from entering and destroying the treated wood.

The polymerisation step may be conducted based on methodology known in the art including subjecting the loaded wood product to temperatures and/or pressures to facilitate polymerisation. In one embodiment the polymerisation step involves hot pressing the resultant wood product derived from the two preceding impregnating steps.

In a preferred embodiment the pH of the wood or non-wood product subjected to the polymerisation step is from about 2-5, and more preferably about 2.

Hot pressing may be conducted under conditions which will effect polymerisation of the 3-FB, advantageously resulting in a three-dimensional chemical adhesive bond between the wood fibers. Preferably, the hot pressing step is conducted at a pressure of from about 5-30 MPa and a temperature of from about 170-200° C. Preferably, the hot pressing step is conducted for a period of from about 5-15 minutes. Such conditions result in the compression of the microstructure of the wood and trigger the polymerisation reaction of furfuryl alcohol from 3-FB.

In a particular embodiment, the final chemically modified wood or non-wood product may have a crushing strength of around 120 MPa, a modulus of elasticity of about 20 GPa and a hardness of around 15,000 N. It will be appreciated however that the engineering properties of the 3-FB treated wood or non-wood will depend on the species, chemical loading and final density. Such parameters can, to some extent, be pre-determined to suit a particular design parameter. The above figures are typical upper limits.

The wood or non-wood product described above, or wood or non-wood when treated by the method of the inventive aspect of the invention advantageously can be sanded or cut into desirable dimensions or shapes. Furthermore, advantageously the wood or non-wood product does not absorb significant amounts of moisture, generally below 6% (based on the weight of the wood product). In this regard, the absorbance of moisture is generally not into the wood cell and, as such, the wood product does not exhibit any substantial amount of swelling or shrinkage during a soaking and drying cycle.

The high modulus of elasticity represents a substantial increase compared with that of the untreated softwood. In particular, typically the parent softwood would have a modulus of elasticity of between 5-6 GPa, compared with that of the treated wood up to about 20 GPa. For instance, about 15 GPa, about 16 GPa, about 17 GPa, about 18 GPa, or about 19 GPa. Similarly, the hardness of the wood product of the invention is significantly higher than that of the parent wood, and is typically much higher than that of any hardwood which is currently available. For example, jarrah has a hardness of around 7000 N, which is much less than that which may be provided according to certain embodiments of the invention.

Still further, the wood or non-wood product of the invention demonstrates high fire resistance, typically in the range of 85-90% of the values which may be expected for fully loaded boron wood. It is also noted that, in general terms, boron can not be successfully fixed to wood, and is thus typically lost from surface treated wood. In contrast, natural heavy hardwoods are generally untreatable and as such as generally not deemed to be fire-resistant. In engineering terms, the wood or non-wood product is structurally sound. In terms of dimensional stability swelling, shrinking and water uptake, the 3-FB treated wood or non-wood products of the present invention are superior compared to natural ebony. Similarly, in economic terms, the production of the wood product, for example, using the process for treating wood described above, is cost effective in that soft wood material may be treated to provide a replacement for the more expensive hardwood materials.

One of the main advantages of the present two step impregnating method involves the initial production of 3-FB and its subsequent impregnation into the softwood. The inventors initially postulated that a similar result could be achieved by impregnating a mixture of 3-furfuryl alcohol and boric acid and forming the 3-FB reagent in situ (i.e., within the wood). However, reaction of 3-furfuryl alcohol and boric acid produces water, which is found to be an inhibitor of the subsequent polymerisation reaction. The present process of separately forming 3-FB and impregnating this reagent overcomes these issues and is also amenable to large scale production of chemically modified wood or non-wood. Accordingly, the 3-FB in this process is not produced in situ within the wood or non-wood. This process also avoids the issues of using furfuryl alcohol which include—incomplete polymerisation, instability, long curing times and short pot life. The resultant wood or non-wood is characterised with superior dimensional stability, low water uptake, is biologically resistant, and has an increased hardness MOE and MOR attractive appearance compared to naturally occurring hardwoods such as ebony and rosewood.

Uses for the chemically modified wood or non-wood products are the same as presently used for natural blackwood (ebony), e.g. musical instruments, artefacts, flooring and paneling, furniture materials, decking and structural materials.

In an embodiment which involves the treatment of Kraft paper, the present invention also provides a process for chemically modifying Kraft paper comprising:
(i) drying the Kraft paper to reduce its moisture content;
(ii) impregnating said Kraft paper with an aqueous composition comprising an acid polymerisation catalyst;
(iii) impregnating the Kraft paper product from step (ii) with 3-FB; and
(iv) subjecting the Kraft paper product from (iii) for a time and under conditions to affect polymerisation of the 3-FB.

Accordingly, the present invention also contemplates a chemically modified non-wood product derived from Kraft paper which has been produced by the polymerisation of 3-furfuryl borate within said Kraft paper.

In an embodiment the process above includes the additional step of:
(v) laminating the Kraft paper product from step (iv) with an epoxy resin.

In another embodiment the present invention contemplates modified Kraft paper products which are derived from the processes mentioned above. In particular the invention contemplates composite Kraft paper products in which two (or more) layers of the modified Kraft paper (in the form of sheets) are sandwiched between concrete or aerated concrete. In an embodiment the modified Kraft paper is in the form of a sheet in a thickness of about 1.0 mm to about 20 mm, for instance about 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, or 19 mm.

The present invention will now be described by way of the following non-limiting Examples.

EXAMPLES

Example 1

Synthesis of 3-FB (3-Furfuryl Borate) (T2 Chemical)

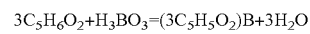

Preparation of 3-FB was conducted in three different scales, 5,000 ml, 20,000 ml and 300 kg.
Procedure as follows:
Charge reaction vessel with required amount of furfuryl alcohol ('2-FM') (Hongye Biochemical Co., Henan, China) at room temperature.
Add required amount of crystalline boric acid, stirring constantly.
Connect to vacuum, minimum −0.098 Mpa. Partial vacuum may cause overheating leading to explosion.
Connect condenser and a receptacle for collection of distillate water.
Start heating. Water will start collecting at 60° C. Temperature should not exceed 85° C.
The reaction vessel is equipped with cooling coil or jacket.
Once the reaction is complete (stochiometric quantity) commence cooling down to under 30° C.

Catalyst Formulation (T1 Solution)
Preparation of Maleic Acid Aqueous Solution.
Procedure as follows:
Fill required quantity of either fresh water or water that was circulated through scrubber in stainless steel tank.
Warm up to 40° C.
Add required amount of maleic acid (Zhengzhou Xingren Chemical Products Co Ltd, Henan, China).
Stir by perculating air or a stirrer for 60 min.

Figure 2:
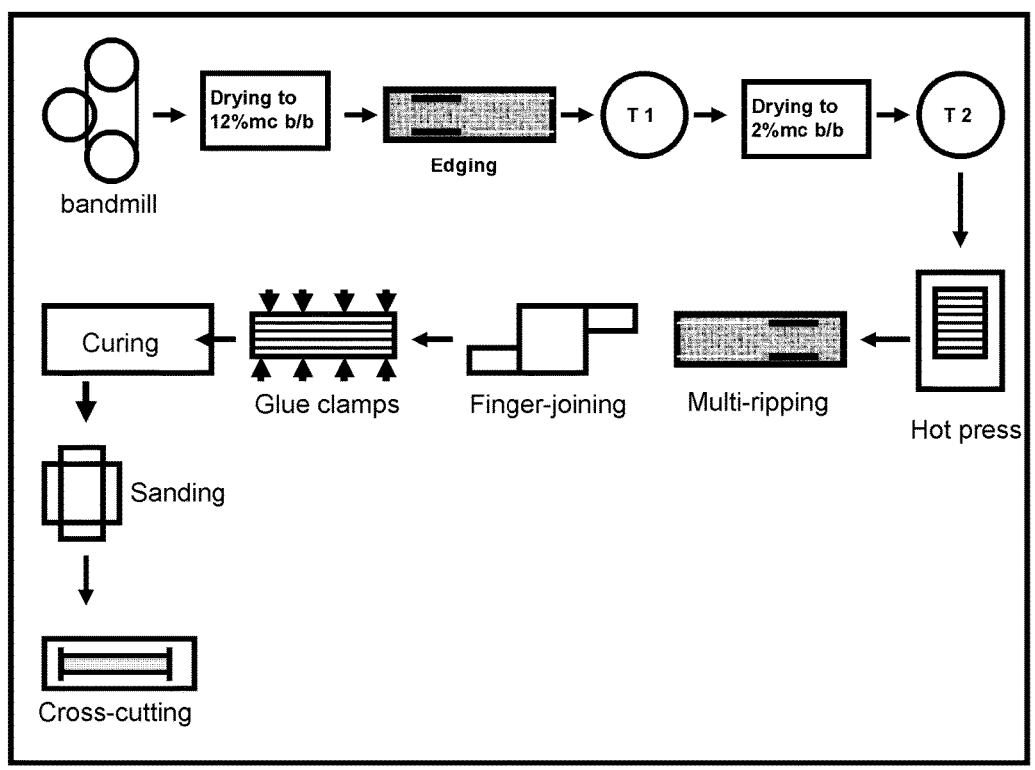
FIG. 2—Diagram depicting a short logs recovery layout of a process according to the present method for the production of, for instance, bench tops, table tops, stair treads, etc. (in 30 and 45 mm).
Figure 3:
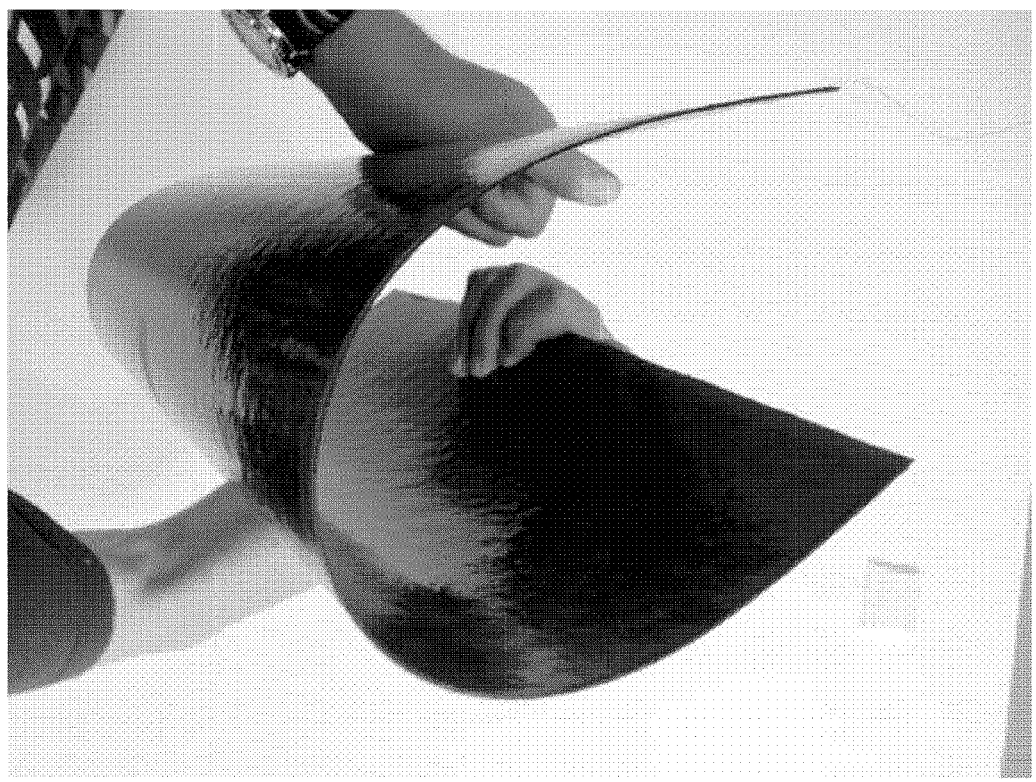
FIG. 3—Photographic representation of a chemically modified non-wood product produced from Kraft paper according to the present invention.
Figure 4:
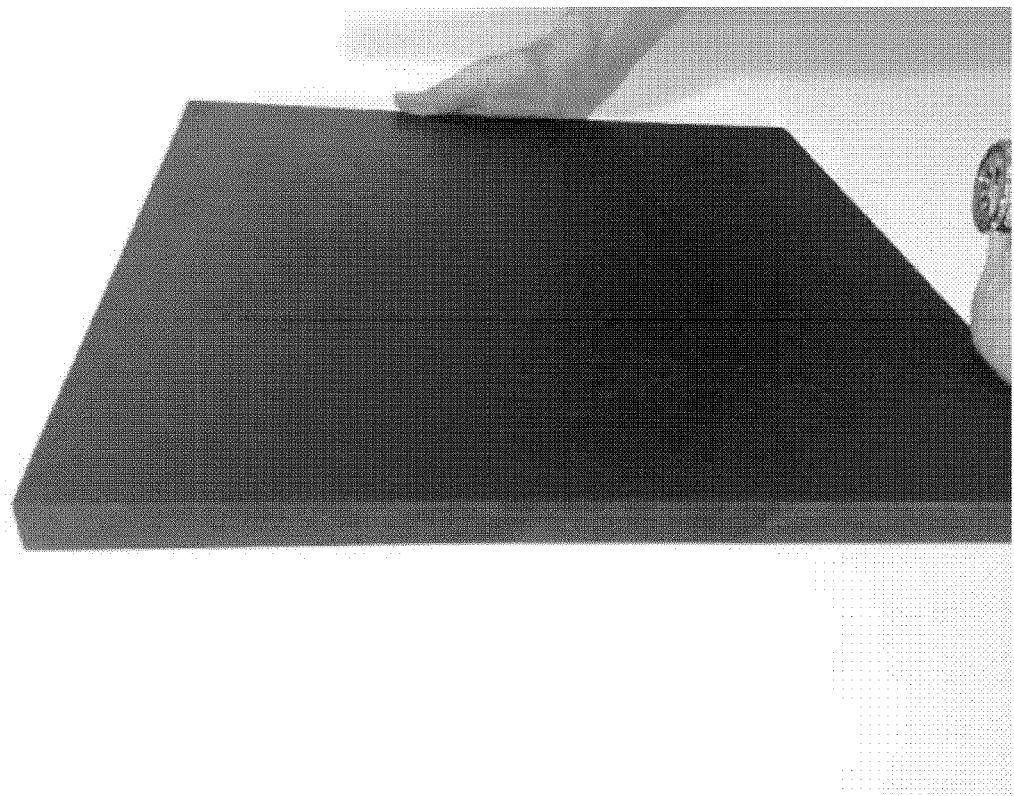
FIG. 4—Photographic representation of a chemically modified non-wood product produced from Kraft paper according to the present invention.
Figure 5:
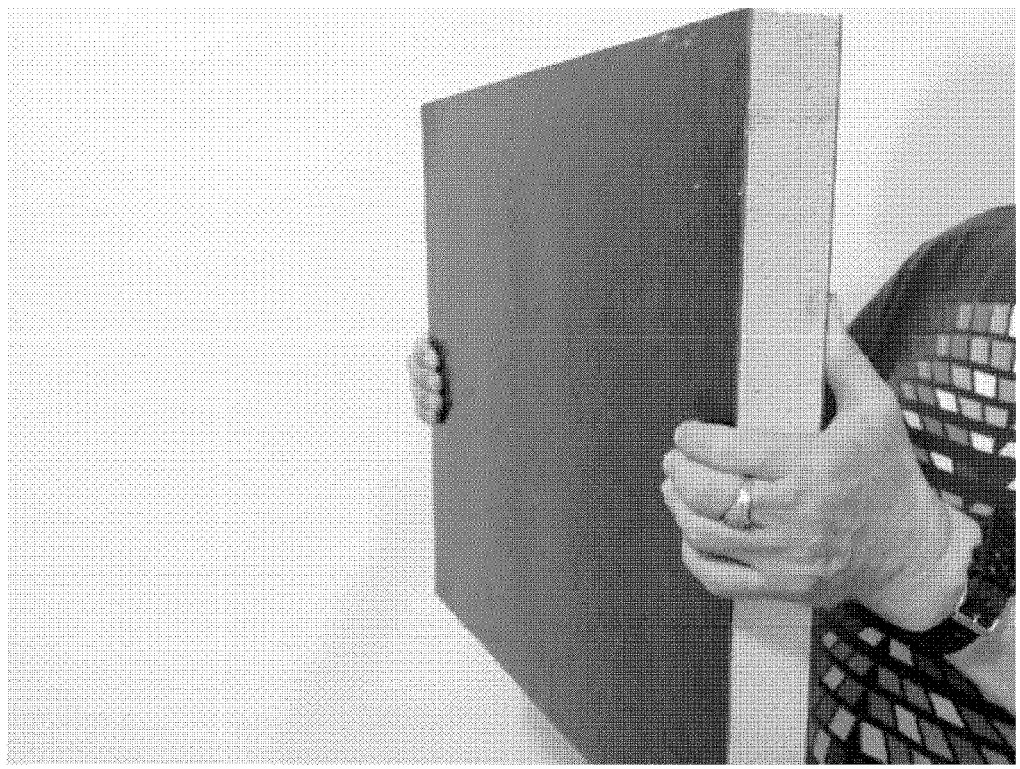
FIG. 5—Photographic representation of a chemically modified non-wood product produced from Kraft paper according to the present invention.

Chemical Modification Process (see FIGS. 1 and 2)
Sawing
Well formed, clear logs are selected and back sawn, bark to bark, sapwood only. The thickness must be pre-calculated on the basis of desired density and product thickness. The heartwood can be either used for different purpose, MW treated and then processed similar to sapwood, or sawn into 4-5 mm thick boards, which can be reconstituted similar to plywood, with T-2 treatment, which acts like plywood resin.
Drying
Sawn sapwood is either stacked and stickered for air drying first, then placed in drying kiln, or put directly through drying process, until moisture content (MC) of 10-12% is reached.
Sizing
Wood was originally sawn bark to bark, and after drying it need to be sized to correct width, according to the specifications of the product.
T-1 Treatment
Sized wood is loaded into the PV-1 pressure vessel, which is then flooded with T-1 solution of 2.5% maleic acid. Vacuum-Pressure-Vacuum cycle is applied to impregnate wood. Duration and values of pressure/vacuum will vary according to wood species, dimensions and desired loading of chemicals. For instance, the vacuum of −0.09 MPa may be applied for 10 minutes to evacuate air contained in the wood. Then the system may be pressurised to 0.2 to 0.4 MPa, depending on desired loading, species and wood size. Final vacuum dries the wood to drip-dry.

Drying

T-1 treated wood is then dried low MC 2-3%. Dryer unit, with dehumidifying capability was used with a capability to reach a low MC.

T-2 Treatment

Dry wood is charged in PV-2 and the vessel is flooded with T-2 treatment chemical. And the cycle of Vacuum-Pressure-Vacuum applied. Duration and pressure vary with the species, desired loading and density, for instance, vacuum of −0.95 MPa for 10 mins, followed by pressure cycle of 5-15 mins at 0.2 to 0.4 MPa.

Hot Pressing

Treated wood is loaded into high-load hot press and gradually pressed to final thickness controlled by sets of spacers and kept at steady temperature until cured. The product coming out of the press is blank blackwood ready for processing to final product after steaming process in pressure vessel, by standard processing methods, sanding edging, sizing and machining.

Steaming

Pressed blackwood is practically at zero moisture, and its EMC (equilibrium moisture content) is about 5%, so it is a good practice to introduce some moisture back into the blackwood, increasing stability in service, reducing internal stresses and washing out small quantities of unreacted chemicals. The condensate is recycled back into T-1 solution, therefore ends up back in the wood.

Testing

Extensive tests were carried in sufficient framework to arrive at reliable and reproducible pattern of behaviour of wood in service:

1. Boron leaching test
2. FA leaching test
3. Water uptake 72 hrs at 20 C
4. Water uptake at 48 hrs at 80 C
5. Swelling at 72 hrs at 20 C
6. Swelling 48 hrs at 80 C
7. Hardness test
8. MOE and MOR.

Boron Leaching Test

Treatment of wood by boron compounds, boric acid, borax etc, remains one of best treatments for wood, being a wide spectrum preservative, effective against insects and fungi. Inherent problems with boron treatment is leacheability of boron compounds in wet conditions. This process offers high boron retention in treated wood.

Procedure

T-1 and T-2 treated wood with known loading of boron compound was tested for leached boric acid. Sample treated as follows:

T-1 treatment 80% w/w with 2.5% water solution of maleic acid w/w.

T-2 treatment 30% with 3-FB, containing 10% boric acid as ester w/w.

Loading of BAE in wood 2.3% w/w.

Standard analytical method AWPA E11-06 for testing leached boric acid was used to determine the amount of leached boric acid, and AWPA A21-93 for determining amount of boric acid retained in wood.

Results

Boric acid leached <10% of the loading.
Boron retention in fully treated wood >90%
Leaching curve from fully treated wood: flat after 1 day Furfuryl Alcohol Leaching Test To ensure stability of blackwood in service, FA leaching test should be a part of routine QC procedure. Essentially, a well cured blackwood shows only traces of unreacted furfuryl alcohol in wood, after 30 days of submersion in water at room temperature by GC analysis. GC is preferred method over HPLC or spectral analysis.

MOE Test

The stiffness of blackwood increases significantly with increase of density, and the desired MOE can be manipulated by level of densification and loading. The range of MOE values range, according to density and loading 10-18 GPa. Higher catalyst loadings will cause brittleness, and lower catalyst loading may result in unreacted furfuryl alcohol.

MOR Test

Similarly, to MOE values for blackwood, MOR also increases from about 40 MPa to a range of 80-120 MPa.

Hardness Test

Hardness of wood is of paramount importance for the products subjected to hard wear and tear, like flooring and decking. Hardness is also a mark of smoothness and appreciated in musical instruments, like finger and fret boards. Testing was done by using standard Janka tool and 20 kN Universal testing machine. The hardness values ranged from 6000 to 15000N.

Tables below give values for the following entities.
Water Uptake 72 hrs at 20 C
Water uptake 48 hrs at 80 C
Tangential Swelling 72 hrs at 20 C
Tangential Swelling 48 hrs at 80 C 72 Hrs Water Immersion at 20° C.

| Sample | Initial MC % | Tangential swelling % | Water uptake % | Hardness N |
|---|---|---|---|---|
| Blackwood (present method) | 6.0 | 0.44 | 21.8 | 9530 |
| Teak | 14.3 | 0.63 | 42.0 | 4230 |
| Merbau | 9.9 | 1.32 | 39.7 | 5560 |
| Oak | 11.9 | 2.02 | 46.5 | 4800 |

Blackwood density 880 kg/m3

48 Hrs Water Immersion at 80° C.

| Sample | Initial MC % | Tangential swelling % | Water uptake % | Hardness N |
|---|---|---|---|---|
| Blackwood (present method) | 6.0 | 0.62 | 24.2 | 9530 |
| Teak | 14.3 | 0.94 | 61.7 | 4230 |
| Merbau | 9.9 | 2.16 | 41.4 | 5560 |
| Oak | 11.9 | 3.88 | 58.9 | 4800 |

Blackwood density 880 kg/m3

Properties of Untreated Wood—Sapwood of *Pinus Radiata*

| Density | 450 kg/m3 |
|---|---|
| Durability | Non-durable Class 5 |
| Dimnsional stability | Low |
| MOE | 3-4 GPa |

-continued

|  |  |
|---|---|
| MOR | 40 MPa |
| Hardness | 3000N |
| Water uptake | >100% |
| Shrinkage (R + T) | 8% |

Properties of Chemically Modified Wood (Blackwood) of the Present Method

|  |  |
|---|---|
| Density | 600-1200 kg/m3 |
| Durability | High H4-H5 |
| Dimensional stability | High |
| MOE | 10-18 GPa |
| MOR | 80-120 MPa |
| Hardness | 6000-15000N |
| Water uptake | 3-20% |
| Shrinkage | None |
| Swelling | 0.3-1.0% |

Termite Test for Blackwood

Specimens of Blackwood prepared by the method disclosed herein were tested for the resistance to termites at James Cook University, Townsville, Australia against two common termite species; Coptotermes and Mastotermes. The exposure of Blackwood samples to the colonies of termites resulted in 100% mortality of the insects and no specimen mass loss.

It is safe to assume that Blackwood is insect resistant, due to:

a. Low moisture content
b. High density
c. Furan polymer inclusion
d. High content of Boron (unleacheable)

Fungal Cellar Test

Samples of Blackwood were tested By CSIRO. Division of Forest Products, Clayton, Australia for its resistance to fungal attack. Specimens were exposed to Brown rot and White rot fungi, resulting in zero mass loss during the trial. It is safe to assume that Blackwood is fungi resistant material, due to same parameters as the insect resistance.

Fire Retardancy Test

There was a simple in-house test for Blackwood behaviour, when exposed to high heat. A simple comparative test indicates that exposure to naked flame Blackwood does not support rapid combustion. It chars slowly without visible flame. The controls of untreated wood combusted rapidly with bright yellow flame. More testing is needed to characterize the level of fire retardancy.

The process according to the present invention can be applied to a wide range of woods, softwoods and hardwoods and non-woods such as bamboo.

Example 2

A process for making a tough, resilient, waterproof and fire resistant material in the form of a thin membrane 1-3.0 mm in thickness.

The process is furan resin treatment of Kraft paper to impart the properties that make this product so outstanding. Very low water uptake, below 10%, from Zero moisture, high tensile strength, hardness, flexural strength, fine grain composition, high density (1400 kg/m3) and unlike wood, it possesses the same strength in all directions The inventor used good quality Kraft packaging paper, treated it with furan resin, then coating it with epoxy resin for tough, hard surface. The material possesses very high tensile strength, exceeding the tensile strength of steel of the same mass and very high degree of elasticity, a perfect material for making composite product sheets. Since all the strength needed for such product is in the strength of a membrane, any material can be sandwiched in with specifications as needed for a set purpose.

Further development includes making lightweight blocks of aggregate of either aerated cement, or a mix of aerated cement and vermiculite and have it sandwiched between two membranes. The product is a perfect material that can be used for thermal insulation of buildings. Panels measuring 2400 mm×1200 mm and 75 mm thick will weigh only 80 kg, that can be easily handled on a building site. Panels are stable, self-supporting and can be used on ceilings, walls and in slightly denser form as flooring substrata. Most buildings in China are very poorly constructed for energy conservation and use of this product can save up to 50% of energy bills, for heating or cooling.

The inventor has tested a range of different building materials for thermal conductivity, and the product proves to be the best of all, resulting in up to 12 deg C. surface temperature difference, compared to standard building material, such as concrete. Time 5 hrs. The specimens were placed on the steel surface, heated to 80° C. and temperature reading were taken in 30 min interval at three levels; 25.0, 50.0, and 70 mm distance from the heated surface.

Noteworthy, lightweight aerated concrete-vermiculite aggregate is crumbling material that cannot be used in self-supporting applications, but sandwiched between 2 sheets of the treated Kraft paper according to the invention it assumes structural properties and self-supporting free

| SPECIES | MC % | Kg/m3 | 72 hrs | swell % | T-1 loading % | Hardness N | Drying efficiency % | MOE Mpa | MOR Mpa |
|---|---|---|---|---|---|---|---|---|---|
| *Shorea* Specie | 14 | 568 | 11.7 | 2.2 | 89.0 | 3233 | 80% | 7805 | 89 |
| Chinese Ash | 13 | 642 | 13.0 | 1.95 | 72.6 | 5344 | 90% | 5941 | 88 |

| SPECIES | BW MOE Mpa | BW MOR Mpa | BW Hardness N | 72 h uptake % | 72 hr Swell % | BW Density Kg/m3 |
|---|---|---|---|---|---|---|
| *Shorea* Specie | 21001 | 155 | 11124 | 11.6 | 0.28 | 1011 |
| Chinese Ash | 18909 | 154 | 12182 | 9.8 | 0.34 | 985 | standing panels may be used as partition walls, ceiling panels and even flooring substrata, providing a high degree of thermal and sound insulation.

|  | 25 mm | 50 mm | 70 mm |
|---|---|---|---|
| Concrete | 68.5 | 59.0 | 53.3 |
| Aerated Concrete | 63.8 | 54.1 | 47.8 |
| Wood (pine) | 62.9 | 50.5 | 43.9 |
| Vermiculite aggregate | 60.7 | 47.2 | 41.3 |

Another variation is a panel made by layering Kraft paper sheets, 20 sheets make 10 mm thick board, and 20 mm will take 40 sheets. There is no limit to the thickness of the panel. Such material can be extensively used in boatbuilding and marine application, ship decks, stairs, and for yacht building, (entire hull and deck). The product may also be amenable for military applications, for example for use in anti-shrapnel products.

Production Steps

Kraft Paper Drying

Kraft paper normally contains 8-12% water, absorbed from air. That water is removed out of the paper prior to 3-FB treatment. It is proposed that the drying be done by MW dryer to minimize distortion and be a continuous process. Assuming 3000 kg/day production, there is 300 kg of water to be removed, or 30 kg/hr.

If paper flows through the system at 10 m/min, 0.5 kg of water needs to be removed per minute. Not a difficult task for MW dryer.

3-FB Impregnation

Dry paper is then put through a double sided glue spreader to coat the paper from both sides Hot Pressing Impregnated Kraft paper is then staked 20 sheets high on each of the 15 plates, separated by non-stick plastic resistant to high temperature. Papers are pressed and heated Epoxy Resin Laminating 3-FB treated and pressed papers are passed through another glue spreader, this time coating papers with epoxy resin into sheets of desired thickness, from 1.0 mm to 20 mm. Stack of such sheets is loaded into cold press and pressed for a period of about 4-5 hours until resin is cured.

Performance

Two types of tests were conducted in order to evaluate the new material and to compare to other products.

Water Tests

Water tests indicate the product's performance in constantly wet condition, as excessive water uptake renders most materials either totally unsuitable or of diminished usefulness.

Water influences biomaterials in several ways; it's is conduit of biohazards, open to fungal and insect attacks, presence of water reduces strength of fibres, thus reducing flexural strength and durability of materials in service is directly related to presence and the content of water.

Long immersion, 30 days, was used to determine the absorption rate of specimen. It is noteworthy, all specimen were dried to Zero MC before treatment, therefore, the water absorption is absolute, not in addition to MC at EMC of about 10-12%.

| KP | P + EPX | P + 3FB 40% | P + 3FB 50% | P + 3FB + EPX1 | P + 3FB + EPX2 |
|---|---|---|---|---|---|
| 150.0 | 27.0 | 9.0 | 4.95 | 8.0 | 5.0 |

It is obvious that the 3-FB treatment alone is responsible for low water absorption, whereas epoxy coating reduces and slows down the absorption. Additionally, visual inspection finds that epoxy only coated paper loses its flexural strength and become soggy, while 3-FB treated specimens retain their initial elasticity and appearance.

Physical Properties

| MOE | 18 GPa |
|---|---|
| MOR | 107 MPa |
| Tensile Strength | 28 MPa |
| hardness | >10 000N |

Unlike wood with its fibres oriented in one direction, the product has wood fibers that are randomly oriented, inherently derived from the Kraft paper making, with strengths that are equally distributed in all directions. This feature makes the product very structurally versatile.

The invention claimed is:

1. A process for chemically modifying wood or non-wood comprising:
   (a) impregnating said wood or non-wood with an aqueous composition comprising an acid polymerisation catalyst;
   (b) impregnating the wood or non-wood product from step (a) with 3-furfuryl borate ('3-FB'); and
   (c) subjecting the wood product from (b) for a time and under conditions to affect polymerisation of the 3-FB, wherein the wood or non-wood consists of the group softwood, bamboo or Kraft paper.

2. The process according to claim 1 wherein the acid polymerisation catalyst is maleic acid.

3. The process according to claim 1 wherein the acid polymerisation catalyst is an aqueous composition comprising 1-10% w/w of the acid polymerisation catalyst.

4. The process according to claim 1 wherein the impregnating step (a) is capable of loading the wood or non-wood with the acid polymerisation catalyst from about 15% to 30% (based on the dry weight of the wood or non-wood).

5. The process according to claim 1 wherein the impregnating step (a) is carried out by a vacuum-pressure-vacuum system.

6. The process according to claim 5 wherein the vacuum-(pressure)-vacuum system is −90 to −95 KPa-(about 200 to about 1,000 KPa)--90 to −95 KPa.

7. The process according to claim 1 wherein the impregnating step (b) is preceded by a drying step to reduce the MC of the wood or non-wood to less than 10%.

8. The process according to claim 7 wherein the impregnating step (b) is conducted so as to facilitate chemical loading of 3-FB of from 15% to 30% (based on the dry weight of the wood or non-wood).

9. The process according to claim 7 wherein the impregnating step (b) is carried out by a vacuum-pressure-vacuum system.

10. The process according to claim 9 wherein the vacuum-pressure-vacuum system is −90 to −95 KPa-(about 200 to about 1,000 KPa)--90 to −95 KPa.

11. The process according to claim 1 wherein step c) involves hot pressing.

12. The process according to claim 1 wherein the wood or non-wood subjected to step c) has a pH of about 2-5.

13. The process according to claim 11 wherein the hot pressing step is conducted at a pressure of from about 5-30 MPa and at a temperature of from about 170-200° C.

14. The process according to claim 1 in which the wood or non-wood product is softwood.

15. The process according to claim 1 in which the wood or non-wood product is bamboo.

16. The process according to claim 1 in which the wood or non-wood product is Kraft paper.

17. A chemically modified wood product derived from softwood which has been produced by the polymerisation of 3-furfuryl borate within said softwood.

18. A chemically modified non-wood product derived from Kraft paper which has been produced by the polymerisation of 3-furfuryl borate within said Kraft paper, wherein the wood or non-wood consists of the group softwood, bamboo or Kraft paper.

19. A chemically modified wood or non-wood product which has been impregnated with 3-furfuryl borate, wherein the wood or non-wood consists of the group softwood, bamboo or Kraft paper.

20. A method of preparing 3-furfuryl borate ('3-FB') comprising the steps of:
   (i) reacting furfuryl alcohol ('2-FM') or 3-furfuryl methanol ('3-FM') with boric acid; and
   (ii) removing water produced during the reaction of (i).

21. A process for chemically modifying Kraft paper comprising:
   (i) drying the Kraft paper to reduce its moisture content;
   (ii) impregnating said Kraft paper with an aqueous composition comprising an acid polymerisation catalyst;
   (iii) impregnating the Kraft paper product from step (ii) with 3-FB; and
   (iv) subjecting the Kraft paper product from (iii) for a time and under conditions to affect polymerisation of the 3-FB.

22. A process according to claim 21 including the additional step of:
   (v) laminating the Kraft paper product from step (iv) with an epoxy resin.

* * * * *